(12) United States Patent
Corzani et al.

(10) Patent No.: US 7,795,476 B2
(45) Date of Patent: Sep. 14, 2010

(54) COMPOSITIONS FOR SUSTAINED RELEASE OF VOLATILE MATERIALS

(75) Inventors: Italo Corzani, Chieti (IT); Calum MacBeath, Francavilla (IT); Manuel Mariani, Montesilvano (IT)

(73) Assignee: The Procter & Gamble Company, Cincinnati, OH (US)

( * ) Notice: Subject to any disclaimer, the term of this patent is extended or adjusted under 35 U.S.C. 154(b) by 695 days.

(21) Appl. No.: 11/194,283

(22) Filed: Aug. 1, 2005

(65) Prior Publication Data

US 2006/0029564 A1 Feb. 9, 2006

(30) Foreign Application Priority Data

Aug. 5, 2004 (EP) ................... 04018573

(51) Int. Cl.
*C07C 43/00* (2006.01)
*A61K 8/00* (2006.01)

(52) U.S. Cl. .......................................... 568/617; 512/2
(58) Field of Classification Search ................. 568/617; 512/2

See application file for complete search history.

(56) References Cited

U.S. PATENT DOCUMENTS

| | | | |
|---|---|---|---|
| 4,678,664 A | | 7/1987 | Schmolka |
| 4,904,524 A | * | 2/1990 | Yoh ............................ 442/61 |
| 5,139,687 A | * | 8/1992 | Borgher et al. .............. 510/515 |
| 6,153,210 A | * | 11/2000 | Roberts et al. .............. 424/411 |
| 6,375,966 B1 | * | 4/2002 | Maleeny et al. ............. 424/405 |
| 2004/0241195 A1 | * | 12/2004 | Tollens ........................ 424/401 |

FOREIGN PATENT DOCUMENTS

| | | |
|---|---|---|
| EP | 1 318 191 A1 | 6/2003 |
| EP | 1 531 169 A1 | 5/2005 |
| WO | WO 02/074430 A1 | 9/2002 |

OTHER PUBLICATIONS

PCT International Search Report, mailed Dec. 2, 2005, 3 pages.

* cited by examiner

*Primary Examiner*—Johann R Richter
*Assistant Examiner*—Ali Soroush
(74) *Attorney, Agent, or Firm*—John M Howell; Jay A Krebs

(57) ABSTRACT

Compositions comprising polytetramethylene glycol and a volatile material (e.g. a perfume) are able to sustainedly release said volatile material and are easy to disperse in liquid and cream products.

13 Claims, No Drawings

COMPOSITIONS FOR SUSTAINED RELEASE OF VOLATILE MATERIALS

FIELD OF THE INVENTION

The present invention relates to compositions of matter which are able to incorporate and sustainedly release volatile materials (e.g. perfumes) based on polytetramethyleneglycol (PTMG). The compositions of the present invention can find a variety of applications wherein a prolonged delivery of a volatile material is desired such as in air freshening devices, deodorants, scented objects, insecticides, detergents, personal care products etc. Compositions according to the present invention are particularly useful in liquid or cream products in which the compositions of the present invention are easily dispersed.

BACKGROUND OF THE INVENTION

A common problem encountered when formulating liquid or cream products which are meant to deliver a volatile material either as their primary function (e.g. perfumes or insecticides) or as their secondary function (e.g. detergents) is to have a sustained release of the volatile material over a long period of time. Another problem is that if the volatile material is a composition formed by several components of different volatility, the more volatile materials tend to evaporate at a much faster rate than the less volatile ones and therefore the release is not balanced, and the delivered volatile composition changes with time.

Prior art attempts to solve this problem are generally based on the use of microcapsules: the volatile material is enclosed in a capsule of polymeric material which is dispersed into the liquid or cream product, said capsules break, dissolve or melt upon product usage due to the intervention of the user. An approach of this type is described e.g. in WO 02/074430 from Quest. This solution is effective in that it allows the delivery of the full perfume bouquet when the capsules are broken or dissolved. On the other hand, the use of capsules for volatile material delivery presents several problems: capsules are difficult to stably disperse in liquids; they tend to leak in the presence of surfactants in the products where they are dispersed, and also they might not break when required thus making it difficult to have a sustained and controlled volatile material release.

EP1318191 from Buck Chemie describes viscous pastes which comprise EO-PO block copolymers and a perfume which are dispersed into water. These compositions still are not satisfactory as they do not have in general a good compatibility with a wide range of volatile materials, particularly perfumes, thus resulting in a lack of flexibility in releasing complex perfumes. Another problem of the compositions described herein is that they are effective when used as such, but when they are incorporated e.g. in a water based product, the copolymers, having strong surfactant properties, tend to form micellar structures in the solution, to interact with the surfactant system, thus dispersing the perfume in the product and losing effectiveness as perfume release control.

Therefore there is a need for a stable system for controlled, balanced and sustained release of volatile materials which can be effectively incorporated in liquid or cream products, in particular cleaning detergent products and personal care products.

The compositions of the present invention can be easily dispersed in liquid or cream products and also allow a balanced release of all components of the volatile material over a long period of time. When the volatile material is a perfume, which is typically composed of many components of different volatility, an additional advantage of the present invention is that, avoiding separation of the components based on their different volatilities, it allows the sustained and balanced delivery of the full perfume character for a long time.

SUMMARY OF THE INVENTION

The present invention relates to a composition comprising:
a) polytetramethylene glycol or a derivative thereof.
b) a volatile material.

DETAILED DESCRIPTION OF THE INVENTION

It was surprisingly found that a composition comprising polytetramethylene glycol or a derivative thereof and a volatile material has the ability of releasing said volatile material for a long time in a sustained manner, i.e. with a long lasting release profile. Such compositions can be advantageously and easily dispersed in liquid and cream products as detergents, beauty care products, personal care products, air fresheners, insect repellants and insecticides and in general whenever sustained release of a volatile material is desired.

Another very important benefit provided by the compositions of the present invention is the possibility to introduce a wide range of volatile materials of a broad polarity range. In fact, compositions according to the present invention have a better compatibility with a broader range of perfume raw materials than prior art solutions.

An additional advantage provided by the compositions of the present invention is that they can be prepared in the form of viscous liquids or pastes at room temperature. This is a particularly desirable property for materials used to incorporate volatile substances as the higher is the processing temperature the bigger is the risk of losing by evaporation significant amounts of the volatile materials incorporated during the manufacturing of the composition.

The first essential component of the composition of the present invention is polytetramethylene glycol (PTMG) or a derivative thereof. PTMG or its derivative can be used at any molecular weight, particularly preferred is a molecular weight from 500 to 3000, more preferably from 1500 to 3000. In general higher molecular weight PTMG will provide compositions which are thicker than those provided by low molecular weight PTMG. Such derivatives exclude copolymers containing as building blocks PTMG and monomers not containing an ether group, such as those described in our copending patent application filed on 14 Nov. 2003 with application number EP 03026234.9.

Also suitable for the present invention are PTMG derivatives. PTMG derivatives are herein defined as those molecules in which PTMG itself constitutes more than 70%, preferably more than 80%, more preferably more than 90% of the total weight of the molecule.

It is in general preferred to use PTMG and not a derivative thereof.

The second essential component of the present invention is a volatile material which is incorporated for subsequent sustained delivery by the compositions of the present invention.

Volatile materials which can be used in the present invention are for example flavors, deodorants, insecticides, pheromones, aromas, repelling agents and most advantageously, perfumes.

The benefits provided by the present invention are particularly relevant when the volatile material is a perfume. Perfumes are typically composed of many components of different volatility. The present invention, owing to the better compatibility of the PTMG with the perfume components, avoids separation of the components based on their different volatility and allows the sustained delivery of the full perfume bouquet for a long time. In a preferred embodiment of the present invention the volatile material is a perfume which is preferably composed by a plurality of components, more preferably by more than 5 components.

As used herein the term perfume means any odoriferous material. In general, such materials are characterised by a vapour pressure less than the atmospheric pressure at room temperatures. The perfumes employed herein will most often be liquid at room temperatures, but also can be solid such as the various camphoraceous perfumes known in the art. A wide variety of chemicals are known for perfumery uses, including materials such as aldehydes, ketones, esters, alcohols, terpenes and the like. Naturally occurring plant and animal oils and exudates comprising complex mixtures of various chemical components are known for use as perfumes, and such materials can be used herein. The perfumes herein can be relatively simple in their composition or can comprise highly sophisticated, complex mixtures of natural and synthetic chemical components, all chosen to provide any desired odor.

Typical perfumes which can be used in the present invention comprise, for example, woody/earthy bases containing exotic materials such as sandalwood oil, civet, patchouli oil and the like. Other suitable perfumes are for example light, floral fragrances, e.g., rose extract, violet extract and the like. Perfumes can be formulated to provide desirable fruity odours, e.g., lime, lemon, orange and the like.

In short, any chemically compatible material which emanates a pleasant or otherwise desirable odour can be used as a perfume in the present invention.

Perfume materials are described more fully in S. Arctander, Perfume Flavors and Chemicals. Vols. I and II. Aurthor, Montclair, N.J., and the Merck Index, 8th Edition, Merck & Co., Inc. Rahway, N.J.

Preferably the volatile material of the present invention is introduced in the compositions of the present invention in a form which allows the chemicals which constitute said volatile material to be chemically dissolved in the matrix comprising PTMG or a derivative thereof. Systems which comprise volatile species covalently bonded to a non volatile one (e.g. pro-perfumes) are not recommended and preferably excluded for use herein as volatile materials according to the present invention. Without being bound to any theory, it is believed that the advantageous properties of the compositions of the present invention can be seen when the volatile material is solubilized in the matrix comprising PTMG or a derivative thereof, as the volatile material release is linked to molecular level interaction between the volatile material and the matrix comprising PTMG or a derivative thereof. Therefore systems which prevent the volatile material from mixing at molecular level with the matrix comprising PTMG or a derivative thereof are not preferred for use in the present invention. These include systems where the perfume oil is encapsulated within a particle or shell and is therefore not able to mix with the PTMG.

Preferably in the compositions of the present invention the ratio PTMG (or a derivative thereof) to volatile material is from 1:10 to 10:1, preferably from 1:3 to 3:1, more preferably from 1:2 to 2:1.

The compositions of the present invention may in addition comprise additional optional components to further improve the processability of the compositions and also the physical properties as well as other characteristics as viscosity and tackiness.

A preferred optional component for the compositions of the present invention is a plasticizer or blend of plasticizers, Suitable plasticizers for use in the compositions according to the present invention include citric acid esters, low molecular weight polyesters, polyethers, liquid rosin esters, aromatic sulfonamides, phthalates, benzoates, sucrose esters, derivatives of polyfunctional alcohols (where polyfunctional means having 2 or more hydroxyl groups), adipates, tartrates, sebacates, esters of phosphoric acid, fatty acids and diacids, fatty alcohols and diols, epoxidized vegetable oils etc and mixtures thereof. The different polarity of the different plasticisers (measurable with any method known to those skilled in the art, for example water/octanol partition coefficient) can be used to tune the polarity of the matrix comprising PTMG or a derivative thereof in order to provide a better match with the polarity of the volatile material, and hence increase compatibility of the matrix with the volatile material. Preferably in the compositions according to the present invention the plasticizer or blend of plasticizers represent between 20 and 80%, more preferably between 30 and 70%, most preferably between 40 and 60% of the total weight of the composition.

Other optional components may include thickeners and viscosity modifiers such as silica, silicates, carbonates, hydroxides, alumina, mica, sulfates, celluloses, starches, acrylic polymers, natural gums, fatty acid salts, liquid rubbers, fatty acid polyamides.

Preferably in the compositions according to the present invention the total amount of PTMG (or a derivative thereof), volatile material and plasticizers (if present), will represent more than 70%, preferably more than 75%, more preferably more than 80% of the total weight of the composition.

The compositions of the present invention can be manufactured by using any known process. A typical process comprises the steps of melting the PTMG (or a derivative thereof) at a temperature around 50° C. and then homogeneously blending the volatile material and the other optional ingredients to form a homogeneous mass that is then cooled to obtain the composition according to the present invention. By using this process the loss of volatile material upon blending, as well as upon subsequent dispersion in finished products is minimized. An additional advantage of a low temperature process is that this allows or simplifies the use of a wider range of volatile materials, for example volatile materials which decompose at higher temperatures or volatile flammable materials which can become explosive at higher temperatures.

The material according to the present invention can be then used as such or, preferably, can be introduced into a cleaning agent or a personal care product which is preferably in liquid, pasty or cream form. The materials of the present invention can be incorporated into said cleaning agent or personal care product by means of common techniques. E.g. the composition according to the present invention can be introduced directly in a surfactant containing product while stirring, thus obtaining an emulsion or a dispersion of fine droplets of said composition according to the present invention. Alternatively, the composition according to the present invention can be premixed with a surfactant solution so as to form a dispersion of fine droplets of said composition according to the present invention into the surfactant solution thus forming a premix. Said premix can then be added to a cleaning agent or personal care product in which said fine droplets of the composition according to the present invention will remain stably dispersed.

Alternatively the compositions of the present invention can also be prepared directly in the form of a dispersion of fine droplets by dispersing a base comprising PTMG or a derivative thereof into a cleaning agent or personal care product comprising at least a surfactant and a volatile material. The PTMG (or derivative) base dispersed in fine droplets will absorb at least a part of the volatile material from said cleaning agent or personal care product thus forming a fine dispersion of droplets of a composition according to the present invention.

Alternatively the composition according to the present invention can introduced in the form of encapsulates. In these systems, the composition is physically entrapped within a solid particle, e.g. a polymeric shell or starch particle.

Further optional ingredients such as other polymers or copolymers, tackifiers, surfactants, fillers, crosslinkers, pigments, dyes, antioxidants and other stabilizers, etc can also be added to provide desired properties to the composition.

The compositions of the present invention are typically waxy solids or viscous liquids which can be readily dispersed in many products, particularly liquid or cream products. The viscosity of the material can be modified introducing thickeners, solvents or rheology modifiers as known in the art.

The compositions of the present invention due to their rheology and to their dispersibility properties are particularly useful to be introduced in liquid or cream products as dispersions. For example a composition according to the present invention can be added to a liquid product comprising surfactants by simply stirring into the product. Alternatively a composition according to the present invention can be dispersed in a surfactant solution and this solution can be then introduced into a liquid or cream product.

Compositions according to the present invention may have different applications whenever the release of a volatile material is desired. For example they can be used in air-freshening devices (room-fresheners, car fresheners, toilet rim-blocks etc.), cleaning/drying systems (tumble dryers, dishwashers, dry cleaning systems etc.), laundry detergents, fabric conditioners, home care products, personal care products (deodorants, anti-perspirants, shampoos, conditioners, body lotions, cosmetics, skin moisturizers, makeup etc.), fine fragrances, scented coatings, films, laminates, hygienic articles (femcare pads, panty liners, diapers, shoe insoles, etc.), scented inks, scented three dimensional objects, disinfectants delivery, insecticides delivery, insect repellants delivery, flavor delivery etc. As said the advantages of the present invention are particularly evident when the compositions according to the present invention are incorporated into liquid or cream products.

The compositions of the present invention will be illustrated with the following examples:

EXAMPLES

Example One 50 parts of Terathane 2000, a poly(tetramethylene glycol) with an average molecular weight of 2000 available from Dupont, 25 parts of Foralyn 5020F, a rosin ester plasticiser available from Eastman Chemical, and 25 parts of benzyl acetate, a perfume raw materials available from Sigma Aldrich were blended together by heating to a temperature above the melting point of the polymer (approximately 40° C.). A homogeneous viscous liquid was obtained. The liquid was cooled down to room temperature and dispersed into a liquid fabric softener product.

Example Two 50 parts of Terathane 2000, a poly(tetramethylene glycol) with an average molecular weight of 2000 available from Dupont and 50 parts of benzyl acetate, a perfume raw materials available from Sigma Aldrich were blended together by heating to a temperature above the melting point of the polymer (approximately 40° C.). A homogeneous viscous liquid was obtained. The liquid was cooled down to room temperature and dispersed into a shampoo.

Example Three

The formula from Example One (30 parts) was heated at 50° C. and then dispersed into a solution of Triton X100 (3 parts), a non-ionic surfactant available from Rohm & Haas, in deionised water (67 parts) to give a stable dispersion with a solids content of 30%. The dispersion was then dispersed into a skin care cream.

Example Four

The formula from Example Two (30 parts) was heated at 50° C. and then dispersed into a solution of Triton X100 (3 parts), a non-ionic surfactant available from Rohm & Haas, in deionised water (67 parts) to give a stable dispersion with a solids content of 30%. The dispersion was then dispersed into a skin care cream.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   a) polytetramethylene glycol or a derivative thereof; and
   b) a volatile material,
   wherein the derivative excludes copolymers of polytetramethylene glycol and monomers which do not contain an ether group; and
   wherein the composition excludes volatile materials encapsulated within a particle or shell.

2. A composition according to claim 1 wherein said volatile material is a perfume.

3. A composition according to claim 1, wherein said composition further comprises a plasticizer or blend of plasticizers.

4. A composition according to claim 1, wherein said polytetramethylene glycol or a derivative thereof and said volatile material comprise greater than about 70% of the total weight of the composition.

5. A composition according to claim 3, wherein said polytetramethylene glycol or a derivative thereof and said volatile material and the plasticizers comprise greater than about 75% of the total weight of the composition.

6. A composition according to claim 1 wherein the ratio between the polytetramethylene glycol or a derivative thereof and the volatile material is from 1:10 to 10:1.

7. A composition according to claim 2 wherein the perfume comprises an aldehyde, a ketone, an alcohol, a terpene or an ester.

8. A composition according to claim 3 wherein said plasticizer is selected form the group consisting of citric acid esters, low molecular weight polyesters, polyethers, rosin esters, aromatic sulfonamides, phthalates, benzoates, sucrose esters, derivatives of polyfunctional alcohols, adipates, tartrates, sebacates, esters of phosphoric acid, fatty acids am diacids, fatty alcohols and diols, epoxidised vegetable oils, and mixtures thereof.

9. A liquid or cream cleaning agent or personal care product comprising a composition according to claim 1; wherein said composition is dispersed or emulsified in it.

10. A process for preparing a liquid or cream cleaning agent or a personal care product comprising the step of dispersing or emulsifying a composition according to claim 1 into said cleaning agent or personal care product.

11. A process for preparing a liquid or cream cleaning agent or a personal care product comprising the step of dispersing or emulsifying a composition comprising polytetramethylene glycol or a derivative thereof into said cleaning agent or a personal care product wherein said cleaning agent or personal care product comprises a volatile material and wherein the derivative excludes copolymers of polytetramethylene glycol and monomers which do not contain an ether group.

12. The composition of claim 1, wherein the polytetramethylene glycol has an average molecular weight ranging from 500 Daltons to 3000 Daltons.

13. The composition of claim 1, wherein the composition comprises a homogeneous blend of polytetramethylene glycol and the volatile material.

* * * * *